(12) United States Patent
Scharf et al.

(10) Patent No.: US 11,013,444 B2
(45) Date of Patent: *May 25, 2021

(54) METHOD AND DEVICE FOR DETERMINING AND PRESENTING SURFACE CHARGE AND DIPOLE DENSITIES ON CARDIAC WALLS

(71) Applicant: Christoph Scharf, Zurich (CH)

(72) Inventors: Christoph Scharf, Zurich (CH); Gunter Scharf, Zurich (CH)

(73) Assignee: Christoph Scharf

( * ) Notice: Subject to any disclaimer, the term of this patent is extended or adjusted under 35 U.S.C. 154(b) by 0 days.

This patent is subject to a terminal disclaimer.

(21) Appl. No.: 16/533,028

(22) Filed: Aug. 6, 2019

(65) Prior Publication Data

US 2020/0187801 A1 Jun. 18, 2020

Related U.S. Application Data

(63) Continuation of application No. 16/014,370, filed on Jun. 21, 2018, now Pat. No. 10,413,206, which is a
(Continued)

(30) Foreign Application Priority Data

Aug. 3, 2006 (CH) ....................... 1251/06

(51) Int. Cl.
*A61B 5/0402* (2006.01)
*A61B 5/283* (2021.01)
(Continued)

(52) U.S. Cl.
CPC ............ *A61B 5/283* (2021.01); *A61B 5/0205* (2013.01); *A61B 5/1075* (2013.01);
(Continued)

(58) Field of Classification Search
CPC ......... A61B 5/04; A61B 5/0408; A61B 5/042; A61B 5/0432; A61B 5/044
See application file for complete search history.

(56) References Cited

U.S. PATENT DOCUMENTS 4,173,228 A 11/1979 Van Steenwyk et al.
5,041,973 A 8/1991 Lebron et al.
(Continued)

FOREIGN PATENT DOCUMENTS

CA 2829626 9/2012
CN 1856123 11/2006
(Continued)

OTHER PUBLICATIONS

Japanese Office Action dated Mar. 10, 2020 issued in corresponding Japanese Application No. 2017-559320, with machine translation to English.
(Continued)

*Primary Examiner* — Allen Porter
(74) *Attorney, Agent, or Firm* — Onello & Mello, LLP (57) ABSTRACT

The invention discloses a method, a system, a computer program and a device for determining the surface charge and/or dipole densities on heart walls. Using the foregoing, a table of dipole densities ν(P', t) and/or a table of surface charge densities ρ(P', t) of a given heart chamber can be generated.

20 Claims, 4 Drawing Sheets

Related U.S. Application Data continuation of application No. 15/435,763, filed on Feb. 17, 2017, now Pat. No. 10,376,171, which is a continuation of application No. 14/865,435, filed on Sep. 25, 2015, now Pat. No. 9,610,024, which is a continuation of application No. 14/547,258, filed on Nov. 19, 2014, now Pat. No. 9,167,982, which is a continuation of application No. 14/189,643, filed on Feb. 25, 2014, now Pat. No. 8,918,158, which is a continuation of application No. 13/858,715, filed on Apr. 8, 2013, now Pat. No. 8,700,119, which is a continuation of application No. 12/376,270, filed as application No. PCT/CH2007/000380 on Aug. 3, 2007, now Pat. No. 8,417,313.

(51) Int. Cl.
| | | |
|---|---|---|
| *G16H 20/60* | (2018.01) | |
| *G16H 20/40* | (2018.01) | |
| *A61B 5/282* | (2021.01) | |
| *A61B 5/287* | (2021.01) | |
| *A61B 5/316* | (2021.01) | |
| *A61B 5/318* | (2021.01) | |
| *A61B 5/333* | (2021.01) | |
| *A61B 5/339* | (2021.01) | |
| *A61B 5/349* | (2021.01) | |
| *A61B 5/363* | (2021.01) | |
| *A61B 5/0205* | (2006.01) | |
| *A61B 5/107* | (2006.01) | |
| *G06F 19/00* | (2018.01) | |
| *G16H 50/50* | (2018.01) | |
| *G16H 20/10* | (2018.01) | |
| *A61B 90/00* | (2016.01) | |

(52) U.S. Cl.
CPC ............ *A61B 5/1076* (2013.01); *A61B 5/282* (2021.01); *A61B 5/287* (2021.01); *A61B 5/316* (2021.01); *A61B 5/318* (2021.01); *A61B 5/333* (2021.01); *A61B 5/339* (2021.01); *A61B 5/349* (2021.01); *A61B 5/363* (2021.01); *G06F 19/00* (2013.01); *G16H 20/10* (2018.01); *G16H 20/40* (2018.01); *G16H 20/60* (2018.01); *G16H 50/50* (2018.01); *A61B 2090/374* (2016.02); *A61B 2090/3762* (2016.02); *A61B 2562/0214* (2013.01)

(56) References Cited

U.S. PATENT DOCUMENTS

| | | |
|---|---|---|
| 5,156,151 A | 10/1992 | Imran |
| 5,293,868 A | 3/1994 | Nardella |
| 5,482,472 A | 1/1996 | Garoni et al. |
| 5,499,981 A | 3/1996 | Kordis |
| 5,555,883 A | 9/1996 | Avitall |
| 5,595,183 A | 1/1997 | Swanson et al. |
| 5,601,084 A | 2/1997 | Sheehan et al. |
| 5,647,367 A | 7/1997 | Lum et al. |
| 5,662,108 A | 9/1997 | Budd et al. |
| 5,722,402 A | 3/1998 | Swanson et al. |
| 5,722,416 A | 3/1998 | Swanson et al. |
| 5,740,808 A | 4/1998 | Panescu et al. |
| 5,749,833 A | 5/1998 | Hakki et al. |
| 5,759,158 A | 6/1998 | Swanson |
| 5,782,239 A | 7/1998 | Webster, Jr. |
| 5,795,298 A | 8/1998 | Vesley et al. |
| 5,795,299 A | 8/1998 | Eaton et al. |
| 5,820,568 A | 10/1998 | Willis |
| 5,830,144 A | 11/1998 | Vesely |
| 5,846,198 A | 12/1998 | Killmann |
| 5,876,336 A | 3/1999 | Swanson et al. |
| 5,928,228 A | 7/1999 | Kordis et al. |
| 5,944,022 A | 8/1999 | Nardella et al. |
| 5,968,040 A | 10/1999 | Swanson et al. |
| 6,014,590 A | 1/2000 | Whayne et al. |
| 6,024,703 A | 2/2000 | Zanelli et al. |
| 6,066,096 A | 5/2000 | Smith et al. |
| 6,086,532 A | 7/2000 | Panescu et al. |
| 6,107,699 A | 8/2000 | Swanson |
| 6,115,626 A | 9/2000 | Whayne et al. |
| 6,187,032 B1 | 2/2001 | Ohyu et al. |
| 6,188,928 B1 | 2/2001 | Noren et al. |
| 6,216,027 B1 | 4/2001 | Willis et al. |
| 6,216,043 B1 | 4/2001 | Swanson et al. |
| 6,240,307 B1 | 5/2001 | Beatty et al. |
| 6,301,496 B1 | 10/2001 | Reisfeld |
| 6,396,198 B1 | 5/2002 | Okimura et al. |
| 6,400,981 B1 | 6/2002 | Govari |
| 6,490,474 B1 | 12/2002 | Willis et al. |
| 6,514,249 B1 | 2/2003 | Maguire et al. |
| 6,574,492 B1 | 6/2003 | Ben-Haim et al. |
| 6,640,119 B1 | 10/2003 | Budd et al. |
| 6,716,166 B2 | 4/2004 | Govari |
| 6,728,562 B1 | 4/2004 | Budd et al. |
| 6,772,004 B2 | 8/2004 | Rudy |
| 6,773,402 B2 | 8/2004 | Govari et al. |
| 6,824,515 B2 | 11/2004 | Suorsa et al. |
| 6,826,420 B1 | 11/2004 | Beatty et al. |
| 6,826,421 B1 | 11/2004 | Beatty et al. |
| 6,839,588 B1 | 1/2005 | Rudy |
| 6,895,267 B2 | 5/2005 | Panescu et al. |
| 6,939,309 B1 | 9/2005 | Beatty et al. |
| 6,950,689 B1 | 9/2005 | Willis et al. |
| 6,970,733 B2 | 11/2005 | Willis et al. |
| 6,978,168 B2 | 12/2005 | Beatty et al. |
| 6,990,370 B1 | 1/2006 | Beatty et al. |
| 7,187,964 B2 | 3/2007 | Khoury |
| 7,187,973 B2 | 3/2007 | Hauck |
| 7,258,674 B2 | 8/2007 | Hillstead et al. |
| 7,263,397 B2 | 8/2007 | Hauck et al. |
| 7,285,119 B2 | 10/2007 | Stewart et al. |
| 7,289,843 B2 | 10/2007 | Beatty et al. |
| 7,291,146 B2 | 11/2007 | Steinke et al. |
| 7,351,914 B2 | 4/2008 | Kaneto et al. |
| 7,479,141 B2 | 1/2009 | Kleen et al. |
| 7,505,810 B2 | 3/2009 | Harlev et al. |
| 7,536,218 B2 | 5/2009 | Govari et al. |
| 7,573,182 B2 | 8/2009 | Savage |
| 7,689,261 B2 | 3/2010 | Mohr et al. |
| 7,766,838 B2 | 8/2010 | Yagi et al. |
| 7,841,986 B2 | 11/2010 | He et al. |
| 7,918,793 B2 | 4/2011 | Altmann et al. |
| 7,953,475 B2 | 5/2011 | Harlev et al. |
| 8,103,327 B2 | 1/2012 | Harlev et al. |
| 8,147,486 B2 | 4/2012 | Honour et al. |
| 8,150,499 B2 | 4/2012 | Gelbart et al. |
| 8,175,680 B2 | 5/2012 | Panescu |
| 8,200,314 B2 | 6/2012 | Bladen et al. |
| 8,208,998 B2 | 6/2012 | Beatty et al. |
| 8,221,411 B2 | 7/2012 | Francischelli et al. |
| 8,233,972 B2 | 7/2012 | Zhang |
| 8,311,613 B2 | 11/2012 | Danehorn |
| 8,320,711 B2 | 11/2012 | Altmann et al. |
| 8,346,339 B2 | 1/2013 | Kordis et al. |
| 8,360,786 B2 | 1/2013 | Duryea |
| 8,364,234 B2 | 1/2013 | Kordis et al. |
| 8,412,307 B2 | 4/2013 | Willis et al. |
| 8,417,313 B2 | 4/2013 | Scharf et al. |
| 8,428,690 B2 | 4/2013 | Li et al. |
| 8,447,377 B2 | 5/2013 | Harlev et al. |
| 8,454,596 B2 | 6/2013 | Ma et al. |
| 8,465,433 B2 | 6/2013 | Zwirn |
| 8,478,388 B2 | 7/2013 | Nguyen et al. |
| 8,512,255 B2 | 8/2013 | Scharf et al. |
| 8,571,647 B2 | 10/2013 | Harlev et al. |
| 8,700,119 B2 | 4/2014 | Scharf et al. |
| 8,755,861 B2 | 6/2014 | Harlev et al. |
| 8,825,130 B2 | 9/2014 | Just et al. |
| 8,825,134 B2 | 9/2014 | Danehorn |
| 8,918,158 B2 | 12/2014 | Scharf et al. |

(56) References Cited

U.S. PATENT DOCUMENTS

| | | |
|---|---|---|
| 8,934,988 B2 | 1/2015 | Persson et al. |
| 8,948,837 B2 | 2/2015 | Harlev et al. |
| 8,968,299 B2 | 3/2015 | Kauphusman et al. |
| 8,979,839 B2 | 3/2015 | De La Rama et al. |
| 8,989,842 B2 | 3/2015 | Li et al. |
| 9,011,423 B2 | 4/2015 | Brewster et al. |
| 9,023,027 B2 | 5/2015 | Bar-Tal et al. |
| 9,026,196 B2 | 5/2015 | Curran et al. |
| 9,031,642 B2 | 5/2015 | Ghosh |
| 9,037,259 B2 | 5/2015 | Mathur |
| 9,044,245 B2 | 6/2015 | Condie et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,220,432 B2 | 12/2015 | Bukhman |
| 9,241,687 B2 | 1/2016 | McGee |
| 9,351,789 B2 | 5/2016 | Novichenok et al. |
| D758,596 S | 6/2016 | Perryman et al. |
| 9,358,398 B2 | 6/2016 | Moffitt et al. |
| 9,380,953 B2 | 7/2016 | Houben et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,498,192 B2 | 11/2016 | Hashimshony et al. |
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| D782,686 S | 3/2017 | Werneth et al. |
| 9,585,588 B2 | 3/2017 | Marecki et al. |
| 9,603,651 B2 | 3/2017 | Ghosh |
| 9,610,024 B2 | 4/2017 | Scharf et al. |
| 9,675,266 B2 | 6/2017 | Afonso et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,730,602 B2 | 8/2017 | Harlev et al. |
| 9,757,044 B2 | 9/2017 | Scharf et al. |
| 9,827,039 B2 | 11/2017 | Dandler et al. |
| 9,901,303 B2 | 2/2018 | Olson |
| 9,913,589 B2 | 3/2018 | Scharf et al. |
| 9,968,268 B2 | 5/2018 | Scharf et al. |
| 10,004,459 B2 | 6/2018 | Werneth et al. |
| 10,028,706 B2 | 7/2018 | Brockway et al. |
| 10,082,395 B2 | 9/2018 | Koyrakh et al. |
| 10,201,311 B2 | 2/2019 | Chou et al. |
| 10,405,828 B2 | 9/2019 | Deladi et al. |
| 2001/0007070 A1 | 7/2001 | Stewart et al. |
| 2002/0026118 A1 | 2/2002 | Govari |
| 2002/0045810 A1 | 4/2002 | Ben-Haim |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0120318 A1 | 6/2003 | Hauck |
| 2003/0153907 A1 | 8/2003 | Suorsa et al. |
| 2003/0158477 A1 | 8/2003 | Panescu |
| 2003/0176799 A1 | 9/2003 | Beatty et al. |
| 2003/0231789 A1 | 12/2003 | Willis et al. |
| 2003/0236466 A1 | 12/2003 | Tarjan et al. |
| 2004/0039312 A1 | 2/2004 | Hillstead et al. |
| 2004/0082870 A1 | 4/2004 | Rudy et al. |
| 2004/0082948 A1 | 4/2004 | Stewart et al. |
| 2004/0254437 A1 | 12/2004 | Hauck et al. |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2006/0244177 A1 | 11/2006 | Kaneto et al. |
| 2007/0016007 A1 | 1/2007 | Govari et al. |
| 2007/0055150 A1 | 3/2007 | Donaldson et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0167722 A1 | 7/2007 | Bladen et al. |
| 2007/0219551 A1 | 9/2007 | Honour et al. |
| 2007/0232949 A1 | 10/2007 | Saksena |
| 2008/0009758 A1 | 1/2008 | Voth |
| 2008/0146937 A1 | 6/2008 | Lee et al. |
| 2008/0287777 A1 | 11/2008 | Li et al. |
| 2008/0319297 A1 | 12/2008 | Danehorn |
| 2009/0024086 A1 | 1/2009 | Zhang et al. |
| 2009/0076483 A1 | 3/2009 | Danehorn |
| 2009/0082691 A1 | 3/2009 | Denison et al. |
| 2009/0131930 A1 | 5/2009 | Gelbart et al. |
| 2009/0143651 A1 | 6/2009 | Kallback et al. |
| 2009/0148012 A1 | 6/2009 | Altmann et al. |
| 2009/0171274 A1 | 7/2009 | Harlev et al. |
| 2009/0264781 A1 | 10/2009 | Scharf et al. |
| 2010/0023004 A1 | 1/2010 | Francischelli et al. |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0256627 A1 | 10/2010 | Ma et al. |
| 2010/0279263 A1 | 11/2010 | Duryea |
| 2010/0286551 A1 | 11/2010 | Harlev et al. |
| 2010/0298690 A1 | 11/2010 | Scharf et al. |
| 2011/0045130 A1 | 2/2011 | Edens et al. |
| 2011/0077526 A1 | 3/2011 | Zwirn |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0144510 A1 | 6/2011 | Ryu et al. |
| 2011/0172658 A1 | 7/2011 | Gelbart et al. |
| 2011/0201951 A1 | 8/2011 | Zhang |
| 2011/0213231 A1 | 9/2011 | Hall et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0123296 A1 | 5/2012 | Hashimshony et al. |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172859 A1 | 7/2012 | Condie et al. |
| 2012/0184863 A1 | 7/2012 | Harlev et al. |
| 2012/0265054 A1 | 10/2012 | Olson |
| 2012/0271138 A1 | 10/2012 | Kordis et al. |
| 2012/0271139 A1 | 10/2012 | Kordis et al. |
| 2012/0277574 A1 | 11/2012 | Panescu |
| 2012/0302912 A1 | 11/2012 | Moffitt et al. |
| 2012/0310064 A1 | 12/2012 | McGee |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |
| 2013/0165916 A1 | 6/2013 | Mathur |
| 2013/0172715 A1 | 7/2013 | Just et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0241929 A1 | 9/2013 | Massarwa et al. |
| 2013/0245433 A1 | 9/2013 | Deladi et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |

(56) References Cited

U.S. PATENT DOCUMENTS

| | | |
|---|---|---|
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0095105 A1 | 4/2014 | Koyrakh et al. |
| 2014/0121470 A1 | 5/2014 | Scharf et al. |
| 2014/0148677 A1 | 5/2014 | Liempde et al. |
| 2014/0180150 A1 | 6/2014 | Scharf et al. |
| 2014/0221803 A1 | 8/2014 | Bar-Tal et al. |
| 2014/0235988 A1 | 8/2014 | Ghosh |
| 2014/0249505 A1 | 9/2014 | Bukhman |
| 2014/0257069 A1 | 9/2014 | Eliason et al. |
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0358143 A1 | 12/2014 | Novichenok et al. |
| 2015/0038862 A1 | 2/2015 | Gijsbers et al. |
| 2015/0196217 A1 | 7/2015 | Harlev et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0223863 A1 | 8/2015 | Ghosh |
| 2015/0257732 A1 | 9/2015 | Ryan |
| 2015/0257825 A1 | 9/2015 | Kelly et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0192902 A1 | 7/2016 | Werneth et al. |
| 2016/0256112 A1 | 9/2016 | Brockway et al. |
| 2017/0035486 A1 | 2/2017 | Lopes et al. |
| 2017/0065204 A1 | 3/2017 | Ludwin et al. |
| 2017/0100049 A1 | 4/2017 | Scharf et al. |
| 2017/0202469 A1 | 7/2017 | Scharf et al. |
| 2017/0258347 A1 | 9/2017 | Scharf et al. |
| 2017/0311833 A1 | 11/2017 | Afonso et al. |
| 2017/0319180 A1 | 11/2017 | Henneken et al. |
| 2018/0055374 A1 | 3/2018 | Scharf et al. |
| 2018/0146948 A1 | 5/2018 | Chou et al. |
| 2019/0159729 A1 | 5/2019 | Chou et al. |

FOREIGN PATENT DOCUMENTS

| | | |
|---|---|---|
| CN | 101048100 | 10/2007 |
| CN | 201223445 | 4/2009 |
| CN | 201275144 | 7/2009 |
| CN | 102770085 | 11/2012 |
| CN | 104462650 | 3/2015 |
| EP | 1166714 | 1/2002 |
| EP | 1760661 | 3/2007 |
| EP | 1779787 | 5/2007 |
| EP | 2051625 | 4/2009 |
| EP | 2252203 | 11/2010 |
| EP | 2683293 | 1/2014 |
| EP | 2953550 | 8/2016 |
| JP | 08501477 | 2/1996 |
| JP | 08504333 | 5/1996 |
| JP | 10137207 | 5/1998 |
| JP | 11504541 | 4/1999 |
| JP | 2000510030 | 8/2000 |
| JP | 2000510250 | 8/2000 |
| JP | 2000358299 | 12/2000 |
| JP | 2001070269 | 3/2001 |
| JP | 2001522288 | 11/2001 |
| JP | 2002051998 | 2/2002 |
| JP | 2002113004 | 4/2002 |
| JP | 2002522106 | 7/2002 |
| JP | 2003511098 | 3/2003 |
| JP | 2004350702 | 12/2004 |
| JP | 2005536313 | 12/2005 |
| JP | 2006511296 | 4/2006 |
| JP | 2008149132 | 7/2008 |
| JP | 2009135109 | 6/2009 |
| JP | 2009136679 | 6/2009 |
| JP | 2011504363 | 2/2011 |
| JP | 2011507656 | 3/2011 |
| JP | 2013188476 | 9/2013 |
| JP | 2014506171 | 3/2014 |
| JP | 2014514031 | 6/2014 |
| JP | 2014516723 | 7/2014 |
| JP | 2016511026 | 4/2016 |
| JP | 2017514553 | 6/2017 |
| WO | 9406349 | 3/1994 |
| WO | 9905971 | 2/1999 |
| WO | 0007501 | 2/2000 |
| WO | 0245608 | 6/2002 |
| WO | 03026722 | 4/2003 |
| WO | 2004026134 | 4/2004 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012068471 | 5/2012 |
| WO | 2012092016 | 7/2012 |
| WO | 2012100184 | 7/2012 |
| WO | 2012100185 | 7/2012 |
| WO | 2012110942 | 8/2012 |
| WO | 2012122517 | 9/2012 |
| WO | 2014124231 | 2/2013 |
| WO | 2013101257 | 7/2013 |
| WO | 2014036439 | 3/2014 |
| WO | 2014130169 | 8/2014 |
| WO | 2014137897 | 9/2014 |
| WO | 2015038607 | 3/2015 |
| WO | 2015148470 | 10/2015 |
| WO | 2016183179 | 11/2016 |
| WO | 2016183285 | 11/2016 |
| WO | 2016183468 | 11/2016 |
| WO | 2017192769 | 11/2017 |
| WO | 2017192775 | 11/2017 |
| WO | 2019144103 | 7/2019 |
| WO | 2019217430 | 11/2019 |

OTHER PUBLICATIONS

Australian Office Action dated Mar. 16, 2020 issued in corresponding Australian Application No. 2016260522.
Japanese Office Action dated Mar. 17, 2020 issued in corresponding Japanese Application No. 2019-071004, with machine translation to English.
Anatomy Warehouse, "Axis Heart Model", 2014, pp. 1-3, at http://www.anatomywarehouse.com/axis-scientific-2-part-deluxe-life-size-human-heart-a-104269. (Year: 2014).
Christoph Scharf et al. Declaration under 37 C.F.R. 1.132, Nov. 15, 2012.
Australian Examination Report dated Feb. 8, 2019 issued in corresponding Australian Application No. 2018250516.
Australian Examination Report dated Jun. 28, 2018 issued in corresponding Australian Patent Application No. 2014318872.
Australian Office Action dated Feb. 26, 2018 issued in Australian Application No. 2017201560.
Australian Office Action dated Jan. 26, 2019 issued in corresponding Australian Application No. 2018211348.
Australian Office Action dated Jul. 6, 2017 issued in corresponding Australian Application No. 2014214756.
Australian Office Action dated Jun. 14, 2018 issued in Australian Application No. 2014214756.
Australian Office Action dated Jun. 27, 2017 issued in corresponding Australian Application No. 2013308531.
Australian Office Action dated Mar. 17, 2018 issued in corresponding Australian Application No. 2013308531.
Australian Office Action dated May 30, 2016 issued in related Australian Application No. 2012225250.

(56) References Cited

OTHER PUBLICATIONS

Australian Office Action dated Sep. 21, 2016 issued in corresponding Australian Application No. 2012225250.
Canadian Office Action dated Apr. 26, 2017 issued in corresponding Canadian Application No. 2932956.
Canadian Office Action dated Apr. 27, 2016 issued in corresponding Canadian Application No. 2747859.
Canadian Office Action dated Dec. 22, 2015 issued in corresponding Canadian Application No. 2656898.
Canadian Office Action dated Jan. 22, 2018 issued in corresponding Canadian Application No. 2932956.
Canadian Office Action dated Mar. 30, 2017 issued in corresponding Canadian Application No. 2747859.
Canadian Office Action dated Nov. 27, 2017 issued in corresponding Canadian Application No. 2829626.
Canadian Office Action dated Nov. 7, 2018 issued in corresponding Canadian Application No. 2932956.
Canadian Office Action dated Oct. 29, 2018 issued in corresponding Canadian Application No. 2829626.
Canadian Office Action dated Oct. 4, 2013 issued in corresponding Canadian Application No. 2659898.
Chinese Office Action dated Apr. 17, 2017 issued in corresponding Chinese Application No. 201480018328.4.
Decision dated Jan. 16, 2018 issued for European Patent Application No. 09702094.5.
Decision dated Jan. 18, 2018 issued for European Patent Application No. 13176658.6.
European Office Action dated Apr. 23, 2018 issued in corresponding European Application No. 07785075.8.
European Office Action dated Apr. 28, 2014 issued in corresponding European Application No. 09702094.5.
European Office Action dated Feb. 29, 2016 issued in corresponding European Application No. 07785075.8.
European Office Action dated Feb. 6, 2019 issued in corresponding European Application No. 14843283.4.
European Office Action dated Jan. 28, 2019 issued in corresponding European Application No. 14748567.6.
European Office Action dated Jan. 31, 2018 issued in corresponding European Application No. 13763151.1.
European Office Action dated Mar. 21, 2017 issued in corresponding European Application No. 07785075.8.
European Office Action dated Mar. 9, 2016 issued in corresponding European Application No. 09702094.5.
European Office Action dated Mar. 9, 2016 issued in corresponding European Application No. 13176658.6.
European Office Action dated Nov. 7, 2017 issued in corresponding European Application No. 15768711.
Extended European Search Report dated Dec. 5, 2018 issued in corresponding European Application No. 16793622.8.
Extended European Search Report dated Jul. 8, 2016 issued in corresponding European Application No. 14748567.6.
Extended European Search Report dated Mar. 14, 2017 issued in corresponding European Application No. 14843283.4.
Extended European Search Report dated Oct. 18, 2017 issued in European Application No. 15768711.
Extended European Search Report dated Oct. 4, 2018 issued in corresponding European Application No. 16793503.0.
Extended European Search Report dated Sep. 29, 2014 issued in corresponding European Application No. 13176658.
International Search Report and Written Opinion dated Apr. 8, 2019, issued in corresponding International Application No. PCT/US19/14498.
International Search Report and Written Opinion dated Aug. 11, 2016 issued in corresponding International Application No. PCT/US2016/032017.
International Search Report and Written Opinion dated Aug. 18, 2016 issued in corresponding International Application No. PCT/US16/32420.
International Search Report and Written Opinion dated Aug. 4, 2017 issued in corresponding International Application No. PCT/US17/30915.
International Search Report and Written Opinion dated Aug. 8, 2016 issued in corresponding European Application No. PCT/US2016/031823.
International Search Report and Written Opinion dated Dec. 12, 2017 issued in corresponding International Application No. PCT/US2017/056064.
International Search Report and Written Opinion dated Jul. 23, 2019 issued in corresponding International Application No. PCT/US2019/031131.
International Search Report and Written Opinion dated Jun. 26, 2015 issued in International Application No. PCT/US2015/022187.
International Search Report and Written Opinion dated Jun. 5, 2014 issued in corresponding International Application No. PCT/US2013/057579.
International Search Report and Written Opinion dated Mar. 10, 2015 issued in corresponding International Application No. PCT/US14/54942.
Extended European Search Report dated Nov. 26, 2019 issued in corresponding European Application No. 19184148.5.
International Search Report and Written Opinion dated Mar. 5, 2013 issued in corresponding International Application No. PCT/US2012/028593.
International Search Report and Written Opinion dated May 20, 2014 issued in corresponding International Application No. PCT/US14/15261.
International Search Report and Written Opinion dated Sep. 25, 2017, issued in corresponding Application No. PCT/US17/30922.
International Search Report dated Oct. 7, 2009 issued in corresponding International Application No. PCT/IB2009/000071.
International Search Report dated Apr. 14, 2008 in related International Application No. PCT/CH2007/000380.
Invitation to Pay Additional Fees issued on Jan. 8, 2014 in corresponding International Application No. PCT/US2013/057579.
Japanese Notice of Allowance dated Feb. 27, 2018 issued in corresponding Japanese Application No. 2015-530101, with English language translation.
Japanese Notice of Allowance dated Jul. 11, 2017 issued in corresponding Japanese Application No. 2013-557-926, with English language summary.
Japanese Notice of Allowance dated Jun. 11, 2019 issued in corresponding Japanese Application No. 2018-024907, with English translation.
Japanese Notice of Allowance dated Mar. 5, 2019 issued in corresponding Japanese Application No. 2018061040, with English translation.
Japanese Notice of Allowance dated Sep. 18, 2018 issued in corresponding Japanese Application No. 2015-557091, with English language translation.
Japanese Office Action dated Aug. 28, 2018 issued in corresponding Japanese Application No. 2016-542062, with machine translation to English.
Japanese Office Action dated Dec. 11, 2018 issued in corresponding Japanese Application No. 2018-024907, with machine translation to English.
Japanese Office Action dated Feb. 16, 2016 issued in corresponding Japanese Application No. 2013-557926, with English translation.
Japanese Office Action dated Feb. 19, 2019 issued in corresponding Japanese Application No. 2016-558799, with machine translation to English.
Japanese Office Action dated Jan. 31, 2017 issued in corresponding Japanese Application No. 2013-557-926, with English language summary.
Japanese Office Action dated Jul. 23, 2019 issued in corresponding Japanese Application No. 2016-542062, with machine translation to English.
Japanese Office Action dated Jun. 27, 2017 issued in corresponding Japanese Application No. 2015-530101, with English language translation.

(56) References Cited

OTHER PUBLICATIONS

Japanese Office Action dated Oct. 10, 2017 issued in corresponding Japanese Application No. 2015-557091, with machine translation to English.
Japanese Office Action dated Sep. 26, 2017 issued in corresponding Japanese Application No. 2017-155346, with English translation.
Della Bella et al. "Non-contact mapping to guide catheter ablation of untolerated ventrical tachycardia" European Heart Journal, May 2002, 23(9)742-752.
Gupta et al. "Point of View Cardiac Mapping: Utility or Futility?", Indian Pacing and Electrophysiology Journal, vol. 2, No. 1, 2002, pp. 20-32.
He et al. "An equivalent body surface charge model representing three-dimensional bioelectrical activity" IEEE Transactions on Biomedical Engineering, 42.7 (Jul. 7, 1995) pp. 637-646.
Jackson, JD, "Surface Distributions of Charges and Dipoles and Discontinuities in the Electric Field and Potential", Classical Electrodynamics, 3rd edition, Dec. 1998, pp. 31-34.
Leif et al., "Geometric modeling based on polygonal meshes". Eurographics 2000 Tutorial, Aug. 21, 2000.
Partial European Search Report dated Apr. 29, 2014 issued in corresponding European Application No. 13176658.
Pullan et al. "The inverse problem of electrocardiology" Northeastern University Electrical and Computer Engineering, Feb. 23, 2007.
Stevenson et al. "Recording Techniques for Clinical Electrophysiology", Journal of Cardiovascular Electrophysiology, vol. 16, No. 9, Sep. 2005, pp. 1017-1022.
Van Oosterom A: "Solidifying the solid angle." 2002 Journal of Electrocardiology 2002 vol. 35 Suppl pp. 181-192 ISSN: 0022-0736.
Wolfgang Nolting: Elektrodynamik-Grundkurs Theoretische Physik 3, Springer Spectrum, p. 89-91.
Japanese Notice of Allowance dated Jul. 7, 2020 issued in corresponding Japanese Application No. 2016558799, with English translation of allowed claims.
Japanese Office Action dated Jun. 30, 2020 issued in corresponding Japanese Application No. 2017559317, with machine translation to English.
Japanese Office Action dated Oct. 15, 2019 issued in corresponding Japanese Application No. 2018-195960, with machine translation to English.
Australian Office Action dated Dec. 22, 2019 issued in corresponding Australian Application No. 2018278959.
Canadian Office Action dated May 20, 2020 issued in corresponding Canadian Application No. 2881457.
European Office Action dated Jun. 15, 2020 issued in corresponding European Application No. 15768711.2.
International Search Report and Written Opinion dated Jul. 21, 2020 issued in corresponding International Application No. PCT/US2020/028779.
Japanese Office Action dated Jul. 28, 2020 issued in corresponding Japanese Application No. 2018-195960, with machine translation to English.
International Search Report and Written Opinion dated Jan. 14, 2020 issued in International Application No. PCT/US2019/060433.
Australian Office Action dated Jan. 15, 2020 issued in corresponding Australian Application No. 2016262547.
Chinese Office Action dated Apr. 8, 2020 issued in corresponding Chinese Application No. 201810153436.2.
Summons to Attend Oral Proceedings dated Dec. 20, 2019 issued in corresponding European Application No. 13763151.1.
Japanese Office Action dated Jan. 7, 2020 issued in corresponding Japanese Application No. 2016-558799, with machine translation to English.
International Search Report and Written Opinion dated Sep. 14, 2020 issued in corresponding International Application No. PCT/US2020/036110.
Japanese Office Notice of Allowance dated Sep. 1, 2020 issued in corresponding Japanese Application No. 2017-559320, with English summary.

METHOD AND DEVICE FOR DETERMINING AND PRESENTING SURFACE CHARGE AND DIPOLE DENSITIES ON CARDIAC WALLS

CROSS REFERENCE TO RELATED APPLICATIONS

The present application is a continuation application of U.S. patent application Ser. No. 16/014,370, filed Jun. 21, 2018, which is a continuation application of U.S. patent application Ser. No. 15/435,763, filed Feb. 17, 2017, which is a continuation application of U.S. patent application Ser. No. 14/865,435, filed Sep. 25, 2015, now U.S. Pat. No. 9,610,024, which is a continuation application of U.S. patent application Ser. No. 14/547,258, filed Nov. 19, 2014, now U.S. Pat. No. 9,167,982, which is a continuation application of U.S. patent application Ser. No. 14/189,643, filed Feb. 25, 2014, now U.S. Pat. No. 8,918,158, which is a continuation application of U.S. patent application Ser. No. 13/858,715, filed on Apr. 8, 2013, now U.S. Pat. No. 8,700,119, which is a continuation application of U.S. patent application Ser. No. 12/376,270, filed on Feb. 3, 2009, now U.S. Pat. No. 8,417,313, which is a 371 national stage application of Patent Cooperation Treaty Application No. PCT/CH2007/000380 filed Aug. 3, 2007, entitled METHOD AND DEVICE FOR DETERMINING AND PRESENTING SURFACE CHARGE AND DIPOLE DENSITIES ON CARDIAC WALLS, which in turn claims priority to Swiss Patent Application 1251/06 filed Aug. 3, 2006, which are incorporated herein by reference.

FIELD OF INVENTION

The invention relates to a method, a system, a computer program and a device for determining the surface charge and/or dipole densities on heart walls in order to locate the origin(s) of cardiac arrhythmias.

BACKGROUND

For localizing the origin(s) of cardiac arrhythmias it is common practice to measure the electric potentials located on the inner surface of the heart by electrophysiological means within the patient's heart. For example, for this purpose electrode catheters can be inserted into the heart and moved around while recording cardiac potentials during normal heart rhythm or cardiac arrhythmia. If the arrhythmia has a regular activation sequence, the timing of the electric activation measured in voltages at the site of the electrode can be integrated when moving the electrode around during the arrhythmia, to create a three dimensional map of the electric activation. By doing this, information on the localization of the source of arrhythmia(s) and mechanisms, i.e., reentry circuits, can be diagnosed to initiate or guide treatment (radiofrequency ablation).

This mapping procedure is often aided by computer systems generating three dimensional maps of catheter positions by localizing the catheter with the help of magnetic fields (the so called Carto System) or transthoracic impedances (by Localisa and NavX). Because all the points of such maps are obtained by electrode positions in contact with the cardiac surface, this mapping system is called contact mapping. It has the inherent limitation that cardiac activation can only be assessed simultaneously at the points in contact with the myocardium. Hence, an instant map of the entire cardiac activation is impossible because the entire heart chamber cannot be contacted without compromising blood circulation. An instant mapping of the simultaneous electric activation of the heart chamber, however, might be of advantage in unstable arrhythmias of short duration, rendering the mapping procedures (moving the electrode around during the arrhythmia) too long. In addition, an instant map of cardiac electric activation might be of advantage during irregular arrhythmias or arrhythmias with non-constant activation sequences that render integration of activation times from contact mapping impossible. Finally, instant maps of cardiac activation are probably also faster and easier obtained, than a contact map generated by time consuming catheters movements to different areas of the heart in all sorts of cardiac arrhythmias.

The disadvantage of contact mapping can be overcome by "non-contact mapping", which allows for mapping cardiac activation of a heart chamber simultaneously without contact to the cardiac wall. For this purpose, for instance, a multi electrode array mounted on an inflatable balloon can be inserted into the heart. The geometry of the heart chamber is obtained either (i) by reconstruction of a contact map, which is obtained from integration of movements with an electrode catheter within the heart chamber, or (ii) by importing imaging data from computed tomography or MRI (magnetic resonance imaging).

Once the geometry of the cardiac chamber is outlined in a map the information of a simultaneous recording of cardiac farfield potentials (unipoles) by the multi electrode array can be extrapolated to the desired cardiac map using advanced mathematical methods. This non-contact mapping has the advantage that it provides the entire electric activation measured by farfield unipolar potentials either in sinus rhythm or during arrhythmia without the need for moving an electrode catheter around the cardiac chamber. This allows for a beat to beat analysis of cardiac activation and, therefore, unstable, irregular or multifocal arrhythmias can be tracked and treated. However, the disadvantage of non-contact mapping is that it relies on farfield potentials, which do not allow for the same precision in localization as contact mapping (i.e. measuring local electrograms (potentials) of cardiac activation by touching the endocardium at the site of interest with a mapping electrode).

Furthermore, non-contact mapping is more prone to artifact generation and interference from potentials generated by cardiac re-polarization and adjacent heart chambers (atria/ventricles). These drawbacks can be overcome to a certain extent with several filtering techniques. One the other side, in many cases these drawbacks also render the localization of cardiac arrhythmias a time-consuming frustrating intervention.

Therefore, the advantages of non-contact mapping, i.e. the instant cardiac activation maps, have to be balanced against the disadvantages, i.e. the decreased spatial resolution due to recording of far field signals, filtering of artifacts, etc.

Finally, another method for the non-invasive localization of cardiac arrhythmias is body surface mapping. In this technique multiple electrodes are attached to the entire surface of the thorax and the information of the cardiac electrograms (surface ECG) is measured in voltages integrated to maps of cardiac activation. Complex mathematical methods are required in order to determine the electric activation in a heart model, for instance, one obtained from CT or MRI imaging giving information on cardiac size and orientation within the thoracic cavity.

The disadvantage of both mapping methods, i.e. contact and non-contact types, is the representation of the electric activity of the heart by means of potentials, that are the result of a summation of electric activities of many cardiac cells. The integration of all these local electric ion charges generated by the cardiac cells provides for the potentials that are measured by current mapping systems.

Therefore, it is an object of the present invention to provide a method, a system, a program and a device for improving precision, accuracy and spatial resolution of cardiac activation mapping, when compared to prior art systems.

SUMMARY OF INVENTION

It was surprisingly found that the use of surface charge and/or dipole densities and in particular their distribution in a heart chamber is a much better indicator of cardiac arrhythmias than electric potentials in the heart.

In a first aspect, the present invention relates to a method for determining a database table of surface charge densities ($\rho$) of at least one given heart chamber, the surface charge density information comprising a table (data values) $\rho(P', t)$, wherein:
  i) the position $P'=(x',y',z')$ of a point at the wall of the heart is defined in x, y, z-coordinates,
  ii) t is the time of measurement for said surface charge density, and
  iii) $\rho$ is the surface charge density at said time t and said position P' derived from a measured electric potential from a given heart chamber,
comprising the following steps:
  a) measuring and/or calculating one or more electric potential(s) $V_e$ in one or more position(s) P at a given time t, and
  b) transforming $V_e$ into said charge density $\rho(P',t)$ by using an algorithm suitable for transforming an electric potential into surface charge density.

In another aspect, the present invention relates to a method for determining a database table of dipole densities $\nu(P',t)$ of at least one given heart chamber, the dipole density information comprising a table (data values) $\nu(P', t)$, wherein:
  i) the position $P'=(x',y',z')$ of a point at the wall of the heart is defined in x, y, z-coordinates,
  ii) t is the time of measurement for said dipole density, and
  iii) $\nu$ is the dipole density at said time t and said position P' derived from a measured electric potential $V_e$ from a given heart chamber,
comprising the following steps:
  a) measuring and/or calculating one or more electric potential(s) $V_e$ in one or more positions P at a given time t, and
  b) transforming $V_e$ into said dipole density $\nu(P',t)$ by using an algorithm suitable for transforming an electric potential into surface charge density.

Preferably, the electric potential(s) $V_e$ can be determined by contact mapping. Equally preferred the electric potential(s) $V_e$ can be determined by non-contact mapping.

In one embodiment, the above mentioned algorithm method for transforming said $V_e$ into surface charge density ($\rho$) or dipole density ($\nu$) in step b) above employs the boundary element method (BEM).

The geometry of the probe electrode can be ellipsoidal or spherical.

In one embodiment, the measured potential(s) $V_e$ can be transformed into surface charge densities $\rho$ using the following equation:

$$V_e(P) = -\frac{1}{4\pi} \int_{S_e} \frac{\rho(P')}{|P' - P|} d\sigma(P') \tag{4}$$

wherein:
  Se=surface of endocardium;
  P'=integration variable running over the entire cardiac wall; and
  P=Position of the measuring electrode.

In another embodiment, the measured potential(s) $V_e$ can be transformed into dipole densities $\nu$ using the following equation:

$$V_e(P) = \frac{1}{4\pi} \int_{S_e} \nu(P') \frac{\partial}{\partial n_{P'}} \frac{1}{|P - P'|} d\sigma(P') \tag{5}$$

wherein:
  Se=surface of endocardium;
  P'=integration variable running over the entire cardiac wall; and
  P=Position of the measuring electrode.

According to a further aspect of the present invention, provided is a system for determining a table of surface charge densities $\rho(P', t)$ of a given heart chamber, comprising:
  a) one unit for measuring and recording at least one electric potential $V_e$ at a given position P,
  b) one a/d-converter for converting the measured electric potentials into digital data,
  c) a processor that transforms the digital voltage data into digital surface charge density data, and
  d) a memory that stores the at least one electric potential $V_e$ and the transformed digital surface charge density data.

In some embodiments, the measuring and recording unit comprises electrodes configured to measure an electric potential $V_e$ when brought into contact with at least one part of the heart chamber.

In some embodiments, the measuring and recording unit comprises electrodes configured to measure an electric potential $V_e$ when not in contact with at least one part of the heart chamber.

The system can also comprise an imaging unit that represents the surface charge densities $\rho(P', t)$ as a 2-dimensional image or time-dependent sequence of images.

The system can comprise an imaging unit that represents the surface charge densities $\rho(P', t)$ as a 3-dimensional image or time-dependent sequence of images.

In accordance with another aspect of the invention, provided is a system that generates a table of dipole densities $\nu(P', t)$ of a given heart chamber, comprising:
  a) a measuring and recording unit that measures and records data used to determine at least one electric potential $V_e$ at a given position P,
  b) an a/d-converter that converts the at least one electric potentials $V_e$ into digital voltage data,
  c) a processor that transforms the digital voltage data into dipole charge density data, and
  d) a memory that stores the at least one electric potential $V_e$ and the transformed dipole charge density data.

The measuring and recording unit can comprise electrodes configured to measure an electric potential $V_e$ when brought into contact with at least one part of the heart chamber.

The measuring and recording unit can comprise electrodes configured to measure an electric potential $V_e$ when not in contact with at least one part of the heart chamber.

The system can further comprise an imaging unit that represents the dipole densities $v(P', t)$ as a 2-dimensional image or time-dependent sequence of images.

The system can further comprise an imaging unit that represents the dipole densities $v(P', t)$ as a 3-dimensional image or time-dependent sequence of images.

The system can be configured to implement the above cited methods of the invention.

In a further aspect, the present invention is directed to a computer program comprising instructions for implementing a method of the present invention.

In a further aspect, the computer program of the invention can comprise instructions implementing a system of the invention.

The computer program of the present invention can comprise a computer readable program code executable by a processor, where the method can include starting program after booting a computer and/or a system in accordance with the invention.

A further aspect of the invention relates to a device for implementing a method according to the invention, comprising at least one an electrode for measuring the electrode potential $V_e$ using the method of contact mapping and/or using the method of non-contact mapping, at least one processing unit for generating and transforming $V_e$ into said surface charge density $\rho(P', t)$ and/or dipole density $v(P', t)$ for presenting on a display.

DETAILED DESCRIPTION OF ILLUSTRATIVE EMBODIMENTS

Research has indicated that the use of the surface charge densities (i.e. their distribution) or dipole densities (i.e. their distribution) to generate distribution map(s) will lead to a more detailed and precise information on electric ionic activity of local cardiac cells than potentials. Surface charge density or dipole densities represent a precise and sharp information of the electric activity with a good spatial resolution, whereas potentials resulting from integration of charge densities provide only a diffuse picture of electric activity. The electric nature of cardiac cell membranes comprising ionic charges of proteins and soluble ions can be precisely described by surface charge and dipole densities. The surface charge densities or dipole densities cannot be directly measured in the heart, but instead must be mathematically and accurately calculated starting from measured potentials. In other words, the information of voltage maps obtained by current mapping systems can be greatly refined when calculating surface charge densities or dipole densities from these.

The surface charge density means surface charge (Coulombs) per unit area ($cm^2$). A dipole as such is a neutral element, wherein a part comprises a positive charge and the other part comprises the same but negative charge. A dipole might represent the electric nature of cellular membranes better, because in biological environment ion charges are not macroscopically separated.

Figure 1:
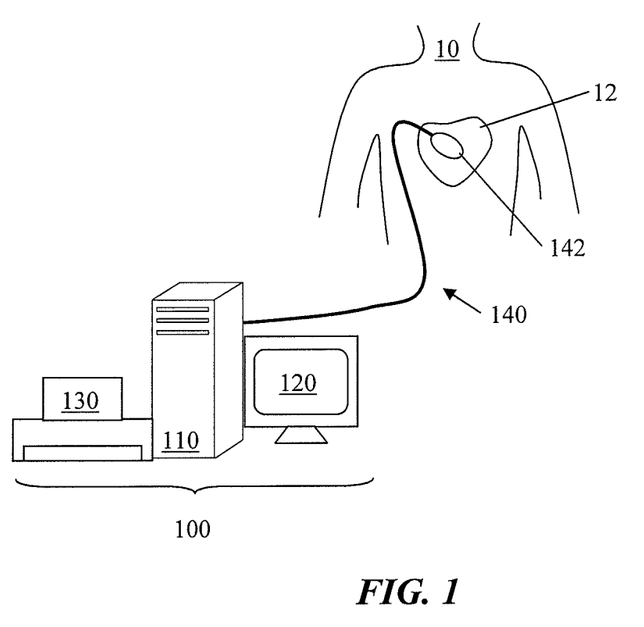
FIG. 1 is an exemplary embodiment of a mapping system, according to aspect of the present invention.

In order to generate a map of surface charge densities (surface charge density distribution) according to the present invention, the geometry of the given heart chamber must be known. The 3D geometry of the cardiac chamber is typically assessed by currently available and common mapping systems (so-called locator systems) or, alternatively, by integrating anatomical data from CT/MRI scans. FIG. 1 shows an example embodiment of a mapping system 100 that can be used to map a heart 12 of a human 10. Mapping system 100 can include a computer 110 having known types of input devices and output devices, such as a display 120 and printer 130, and a probe system 140. For the measurement of potentials the non-contact mapping method a probe electrode 142 will be used, which is connected to the computer 110 via a cable and forms part of probe system 140. The probe electrode 142 may be a multi-electrode array with elliptic or spherical shape. The spherical shape has certain advantages for the subsequent data analysis. But also other types or even several independent electrodes could be used to measure $V_e$. For example, when considering, for example, the ventricular cavity within the endocardium and taking a probe electrode with a surface $S_P$, which is located in the blood, it is possible to measure the potential $V(x,y,z)$ at point $x,y,z$ on the surface $S_P$. In order to calculate the potential at the endocardial surface $S_e$ the Laplace equation:

$$\Delta V = \left(\frac{\partial^2}{\partial x^2} + \frac{\partial^2}{\partial y^2} + \frac{\partial^2}{\partial z^2}\right)V = 0 \qquad (1)$$

needs to be solved, wherein V is the potential and $x,y,z$ denote the three dimensional coordinates. The boundary conditions for this equation are $V(x,y,z)=V\rho(x,y,z)$ on $S_P$, wherein $V_P$ is the potential on surface of the probe.

The solution is an integral that allows for calculating the potential $V(x'y'z')$ at any point $x'y'z'$ in the whole volume of the heart chamber that is filled with blood. For calculating said integral numerically a discretisation of the cardiac surface is necessary and the so called boundary element method (BEM) has to be used.

The boundary element method is a numerical computational method for solving linear integral equations (i.e. in surface integral form). The method is applied in many areas of engineering and science including fluid mechanics, acoustics, electromagnetics, and fracture mechanics.

The boundary element method is often more efficient than other methods, including the finite element method. Boundary element formulations typically give rise to fully populated matrices after discretisation. This means, that the storage requirements and computational time will tend to grow according to the square of the problem size. By contrast, finite element matrices are typically banded (elements are only locally connected) and the storage requirements for the system matrices typically grow quite linearly with the problem size.

With the above in mind, all potentials $V_P$ (x1',y1',z1') on the surface of the probe can be measured. To calculate the potential $V_e$ on the wall of the heart chamber, the known geometry of the surface of the heart chamber must be divided in discrete parts to use the boundary element method. The endocardial potentials $V_e$ are then given by a linear matrix transformation T from the probe potentials $V_P$: $V_e = T\, V_P$.

After measuring and calculating one or more electric potential(s) $V_e$ of cardiac cells in one or more position(s) P(x,y,z) of the at least one given heart chamber at a given time t. The surface charge density and the dipole density is related to potential according to the following two Poisson equations:

$$\Delta V_e = \rho(P)\delta_{S_e}(P) \qquad (2)$$

$$\Delta V_e = \frac{\delta}{\partial n}(\upsilon \delta_{S_e}(P)) \qquad (3)$$

wherein ρ(P) is the surface charge density in position P=x,y,z, $\delta_{S_e}(P)$ is the delta-distribution concentrated on the surface of the heart chamber $S_e$ and υ is the dipole density.

There is a well known relationship between the potential $V_e$ on the surface of the wall of the heart chamber and the surface charge (4) or dipole densities (5).

$$V_e(P) = -\frac{1}{4\pi}\int_{S_e}\frac{\rho(P')}{|P'-P|}d\sigma(P') \qquad (4)$$

$$V_e(P) = \frac{1}{4\pi}\int_{S_e}\upsilon(P')\frac{\partial}{\partial n_{P'}}\frac{1}{|P-P'|}d\sigma(P') \qquad (5)$$

(For a review see Jackson J D. Classical Electrodynamics, $2^{nd}$ edition, Wiley, New York 1975.)

The boundary element method again provides a code for transforming the potential $V_e$ in formulas 4 and 5 into the desired surface charge densities and dipole densities, which can be recorded in the database.

In another embodiment of the method of the present invention the electric potential(s) $V_e$ is (are) determined by contact mapping. In this case the steps for calculating the electric potential $V_e$ are not necessary, because the direct contact of the electrode to the wall of the heart chamber already provides the electric potential $V_e$.

In a preferred embodiment of the method of the present invention the probe electrode comprises a shape that allows for calculating precisely the electric potential $V_e$ and, thus, simplifies the calculations for transforming $V_e$ into the desired charge or dipole densities. This preferred geometry of the electrode is essentially ellipsoidal or spherical.

In order to employ the method for determining a database table of surface charge densities of at least one given heart chamber in the context of the present invention, it is preferred to use a system comprising at least:
 a) one unit for measuring and recording electric potentials V at a given position P(x,y,z) on the surface of a given heart chamber (Contact mapping) or a probe electrode positioned within the heart, but without direct wall contact (noncontact mapping)
 b) one a/d-converter for converting the measured electric potentials into digital data,
 c) one memory to save the measured and/or transformed data, and
 d) one processor unit for transforming the digital data into digital surface charge density or dipole density data.

It is noted that numerous devices for localising and determining electric potentials of cardiac cells in a given heart chamber by invasive and non-invasive methods are well known in the art and have been employed by medical practitioners over many years. Hence, the method, system, and devices of the present invention do not require any particular new electrodes for implementing the best mode for practicing the present invention. Instead, the invention provides a new and advantageous processing of the available data that will allow for an increase in precision, accuracy and spatial resolution of cardiac activation mapping when compared to prior art systems based on electric surface potentials in the heart only. In the near future, the present invention will allow for providing superior diagnostic means for diagnosing cardiac arrhythmias and electric status of heart cells including metabolic and functional information.

Figure 2:
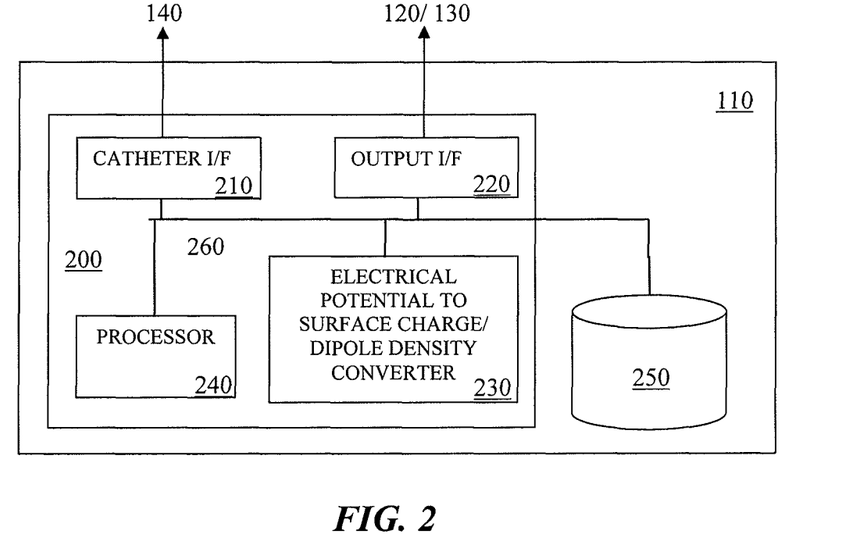
FIG. 2 is an exemplary embodiment of a computer architecture forming part of the mapping system of FIG. 1.

FIG. 2 provides an example embodiment of a computer architecture 200 that can form part of mapping system 100. Architecture 200 includes standard interface modules 210 for probe system 140 (and electrode 142) and standard interface modules 220 for interfacing with output devices 120, 130. The computer includes at least one processor 240 and at least one computer memory 250. The foregoing are generally known, however the present invention further includes an electrical potential to surface charge density and/or dipole density converter module 230. Module 230 includes instructions necessary for carrying out the methods described herein, when executed by processor 240, wherein the results of such processing are stored in memory 250—as would be understood by one skilled in the art having the benefit of this disclosure.

Figure 3:
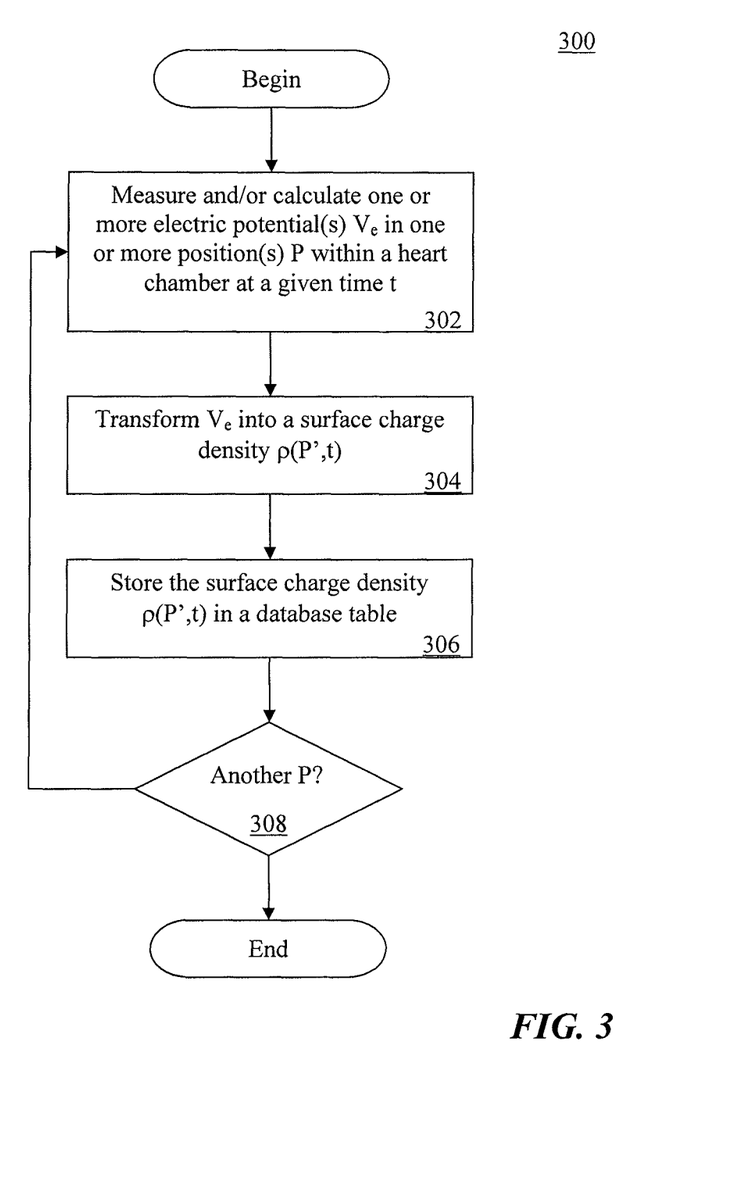
FIG. 3 is an example embodiment of a method of determining and storing surface charge densities, in accordance with aspects of the present invention.
Figure 4:
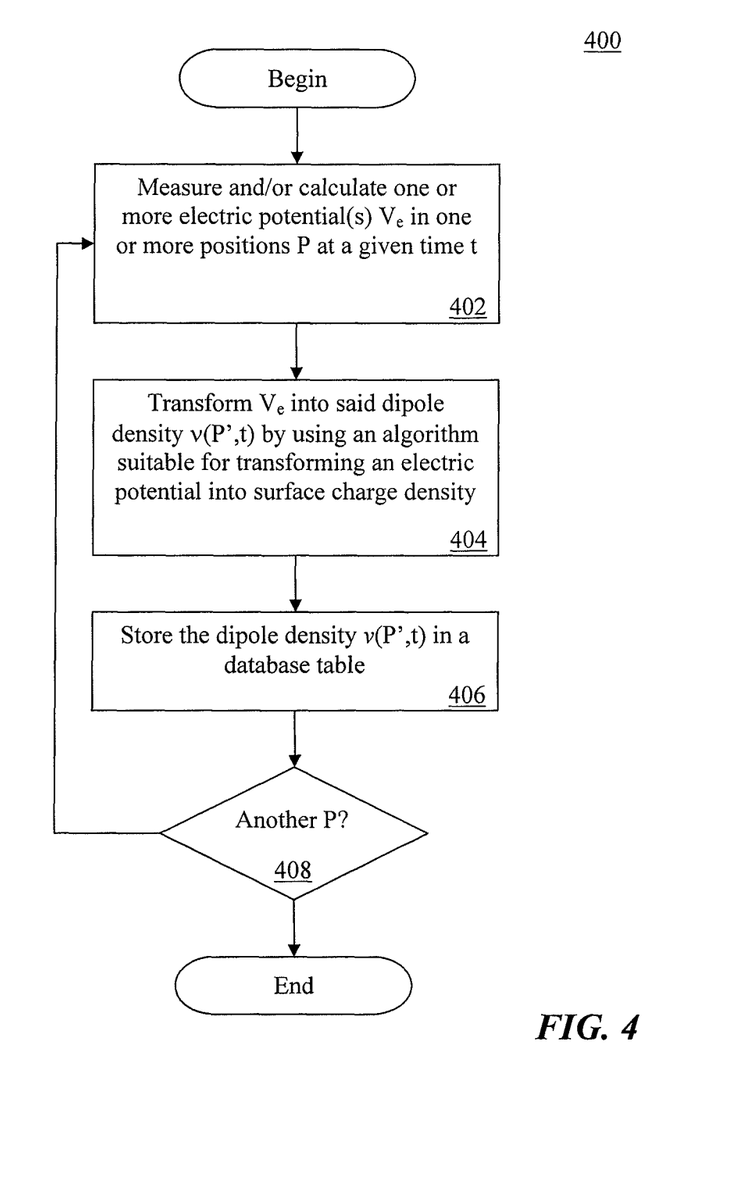
FIG. 4 is an example embodiment of a method of determining and storing dipole densities, in accordance with aspects of the present invention.

FIG. 3 and FIG. 4 summarize methods for determining and storing surface charge densities and dipole densities in accordance with aspects of the present invention, respectively, which have been described in detail above.

In method 300 of FIG. 3, in step 302, mapping system 100 is used to measure and/or calculate one or more electric potential(s) $V_e$ into one or more position(s) P within a heart chamber at a given time t. In step 304, $V_e$ is transformed into a surface charge density ρ(P',t). In step 306, the surface charge density ρ(P',t) is stored in a database table. The method is repeated if there is another P, in step 308.

In method 400 of FIG. 4, in step 402, mapping system 100 is used to measure and/or calculate one or more electric potential(s) $V_e$ in one or more position(s) P within a heart chamber at a given time t. In step 404, $V_e$ is transformed into said dipole density ν(P',t) by using an algorithm suitable for transforming an electric potential into surface charge density. In step 406, the dipole density ν(P',t) is stored in a database table. The method is repeated if there is another P, in step 408.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

What is claimed is:

1. A cardiac mapping system, comprising:
 a plurality of electrodes configured to sense and/or record electrical activity of at least one heart chamber, including:
  a first set of electrodes configured to record a first set of electric potentials when in contact with a surface of the at least one heart chamber; and a second set of electrodes configured to record a second set of electric potentials when not in contact with a surface of the at least one heart chamber; and
at least one processor configured to:
transform the first and second sets of electric potentials into a continuum of cellular membrane dipole density data and/or surface charge data, and
generate information to display the continuum as a map of charge densities across an endocardium of the at least one heart chamber.

2. The system of claim 1, wherein the first set of electrodes includes a plurality of electrodes arranged in an ellipsoidal geometry.

3. The system of claim 1, wherein the first set of electrodes includes a plurality of electrodes arranged in a spherical geometry.

4. The system of claim 1, wherein the second set of electrodes includes one or more electrodes adapted to be placed on a skin surface of a thorax.

5. The system of claim 1, wherein the at least one processor is further configured to execute a set of transformation instructions stored in a computer memory.

6. The system of claim 5, wherein the transformation instructions include rules to employ a boundary element method (BEM) to transform the first and second sets of electric potentials into cellular membrane dipole density data.

7. The system of claim 6, wherein the at least one processor employs the BEM to perform a discretisation of the endocardium.

8. The system of claim 6, wherein the at least one processor employs the transformation instructions to implement rules that transform measured potentials $V_e$ from the first and/or second sets of electric potentials into surface charge densities $\rho$ according to the following equation:

$$V_e(P) = -\frac{1}{4\pi}\int_{S_e} \frac{\rho(P')}{|P'-P|} d\sigma(P')$$

wherein:
Se=surface of endocardium;
P'=integration variable running over an entire cardiac wall; and
P=Position of the at least one electrode in contact with a surface of the heart or the at least one electrode not in contact with a surface of the heart.

9. The system of claim 6, wherein the at least one processor employs the transformation instructions to implement rules that transform measured potentials $V_e$ from the first and/or second sets of electric potentials into dipole densities $\nu$ according to the following equation:

$$V_e(P) = \frac{1}{4\pi}\int_{S_e} \nu(P')\frac{\partial}{\partial n_{P'}} \frac{1}{|P-P'|} d\sigma(P')$$

wherein:
Se=surface of endocardium;
P'=integration variable running over an entire cardiac wall; and
P=Position of the at least one electrode in contact with a surface of the heart or the at least one electrode not in contact with a surface of the heart.

10. The system of claim 1, wherein the at least one processor is configured to execute a set of map generation instructions stored in a computer memory.

11. The system of claim 1, wherein the processor is configured to drive at least one display to render a graphical representation of the cellular membrane dipole density data and/or surface charge data in association with a graphical representation of the heart.

12. The system of claim 1, wherein the processor is configured to drive at least one display to render a map of dipole densities and/or surface charge densities as a 2-dimensional image.

13. The system of claim 1, wherein the processor is configured to drive at least one display to render a map of dipole densities and/or surface charge densities as a 3-dimensional image.

14. The system of claim 1, wherein the processor is configured to drive at least one display to render a map of dipole densities and/or surface charge densities as a time-dependent sequence of images.

15. The system of claim 1, wherein the continuum is a continuum of cellular membrane dipole density data.

16. The system of claim 1, wherein the continuum is a continuum of cellular membrane surface charge data.

17. The system of claim 1, wherein the at least one processor is configured to determine the continuum of cellular membrane dipole density data and/or surface charge density data at a set of positions P' as a 3-dimensional image, a 2-dimensional image, or a time-dependent sequence of images, or a combination of one or more thereof.

18. The system of claim 1, wherein the first set of electrodes and the second set of electrodes are configured to sequentially record their respective potentials.

19. The system of claim 1, wherein the first set of electrodes and the second set of electrodes are configured to simultaneously record their respective potentials.

20. The system of claim 1, further comprising:
a probe system configured to record the first and second sets of electric potentials at given positions P on a cellular membrane of the endocardium of the at least one heart chamber.

* * * * *